(12) United States Patent
Burkhart et al.

(10) Patent No.: US 6,417,179 B1
(45) Date of Patent: Jul. 9, 2002

(54) EAR WAX SOLUTION

(76) Inventors: Craig G. Burkhart; Craig N. Burkhart, both of 4556 Crossfields Rd., Toledo, OH (US) 43623

( * ) Notice: Subject to any disclaimer, the term of this patent is extended or adjusted under 35 U.S.C. 154(b) by 0 days.

(21) Appl. No.: 09/986,237

(22) Filed: Oct. 22, 2001

Related U.S. Application Data

(63) Continuation-in-part of application No. 09/416,782, filed on Oct. 13, 1999.
(60) Provisional application No. 60/104,089, filed on Oct. 13, 1998, and provisional application No. 60/109,826, filed on Nov. 25, 1998.

(51) Int. Cl.[7] .......................... A61K 31/56; A61K 9/66
(52) U.S. Cl. ........................ 514/178; 424/455
(58) Field of Search ........................... 424/455; 514/178

(56) References Cited

U.S. PATENT DOCUMENTS 3,422,186 A * 1/1969 Sasmor
5,954,682 A * 9/1999 Petrus
6,251,428 B1 * 6/2001 Yoo

OTHER PUBLICATIONS

Meyer et al., Effect of otic medications containing . . . , Database Hcaplus, AN1990:152079, abstract, J. Am. Vet. <ed. Assoc. 1990, vol. 196(5), 743–4.*

* cited by examiner

*Primary Examiner*—William R. A. Jarvis
*Assistant Examiner*—Vickie Kim
(74) *Attorney, Agent, or Firm*—MacMillan, Sobanski & Todd, LLC

(57) ABSTRACT

An ear wax solution includes a detergent which is effective to treat the ear wax by a mechanism involving at least one of dissolving the ear wax, softening the ear wax, and reducing the attachment of the ear wax to the ear. The detergent is selected from anionic detergents, cationic detergents, zwitterionic detergents, ampholytic detergents, amphoteric detergents, nonionic detergents having a steroid skeleton, or mixtures thereof. The ear wax solution also includes a solvent which is water, a hydrophilic solvent, or a mixture thereof The ear wax solution also includes an alkaline material effective to make the solution alkaline. The ear wax solution further includes an ionic additive effective to increase the ionic strength of the solution.

13 Claims, No Drawings

EAR WAX SOLUTION

CROSS-REFERENCE TO RELATED APPLICATIONS

This application claims the benefit of provisional application Serial No. 60/104,089, filed Oct. 13, 1998 and Serial No. 60/109,826, filed Nov. 25, 1998, and this application is a continuation-in-part of Ser. No. 09/416,782, filed Oct. 13, 1999.

FIELD OF INVENTION

This invention relates to treatments for ear wax, and in particular to an improved ear wax solution.

BACKGROUND OF THE INVENTION

Ear wax is produced by ceruminous glands, sebaceous glands, keratinocytes, and hair from the outer third of the human ear canal. Ear wax is composed of lipid coated epidermal cells, lipids, proteins and carbohydrates. It is very hydrophobic and not soluble in water. Ear wax functions as a protectant to the inner ear from infection, as well as a cleaning and lubricating agent for the external ear canal. However, accumulation and impaction of ear wax can cause itching, pain, hearing loss, perforated tympanum, tinnitis, dizziness, and increased risk of infection. Approximately 150,000 ear wax removals are performed weekly in America due to such otologic complications. Impaction of ear wax is the most common otologic problem encountered by physicians. It can affect up to 6% of the general population, and 20% of the geriatric population.

Excessive ear wax is often removed in physicians' offices using mechanical methods. A number of solutions have also been tried to help remove ear wax. Organic based solutions prove not to be very helpful as they appear only to soften the ear wax. Interestingly, water by itself proves to be partially effective. Alkaline solutions (e.g., solutions containing sodium bicarbonate) are somewhat more effective. However, there is still a need for an improved ear wax solution.

SUMMARY OF THE INVENTION

This invention relates to an improved ear wax solution. The ear wax solution includes a detergent which is effective to treat the ear wax by a mechanism involving at least one of dissolving the ear wax, softening the ear wax, and reducing the attachment of the ear wax to the ear. The detergent is selected from anionic detergents, cationic detergents, zwitterionic detergents, ampholytic detergents, amphoteric detergents, nonionic detergents having a steroid skeleton, or mixtures thereof. The ear wax solution also includes a solvent which is water, a hydrophilic solvent, or a mixture thereof. The ear wax solution also includes an alkaline material effective to make the solution alkaline. The ear wax solution further includes an ionic additive effective to increase the ionic strength of the solution.

In another embodiment, the ear wax solution includes a detergent comprising a salt of a bile acid, the detergent being effective to treat the ear wax by a mechanism involving at least one of dissolving the ear wax, softening the ear wax, and reducing the attachment of the ear wax to the ear. The ear wax solution also includes a solvent which is water, a hydrophilic solvent, or a mixture thereof. The ear wax solution also includes an alkaline material effective to make the solution alkaline.

In another embodiment of the invention, an ear wax formulation comprises a detergent, a polymer, and a solvent. The detergent is effective to treat the ear wax by a mechanism involving at least one of dissolving the ear wax, softening the ear wax, and reducing the attachment of the ear wax to the ear. The detergent is selected from anionic detergents, cationic detergents, zwitterionic detergents, ampholytic detergents, amphoteric detergents, nonionic detergents having a steroid skeleton, or mixtures thereof. The polymer is effective to enhance the treatment by a mechanism involving at least one of reducing the irritancy of the detergent on the ear canal, and increasing the retention of the formulation in the ear canal and thereby reducing absorption of the formulation into the epidermal tissues of the ear canal. The solvent is water, a hydrophilic solvent, or a mixture thereof.

In a preferred embodiment of the invention, the ear wax solution includes one or more materials that enhance miscelle formation by the detergent. The formation of miscelles by the detergent optimizes the effectiveness of the ear wax solution.

In another preferred embodiment of the invention, the ear wax solution contains a plurality of detergents effective to treat the ear wax by a mechanism involving at least one of dissolving the ear wax, softening the ear wax, and reducing the attachment of the ear wax to the ear. In some instances the use of two or more detergents together significantly improves the effectiveness of the ear wax solution.

The invention also relates to a method for removing ear wax from an ear. In a first step of the method, an ear wax solution is inserted into the ear in contact with the ear wax, the ear wax solution comprising: (a) a detergent effective to treat the ear wax by a mechanism involving at least one of dissolving the ear wax, softening the ear wax, and reducing the attachment of the ear wax to the ear, the detergent being selected from the group consisting of anionic detergents, cationic detergents, zwitterionic detergents, ampholytic detergents, amphoteric detergents, nonionic detergents having a steroid skeleton, and mixtures thereof, and (b) a solvent selected from the group consisting of water, hydrophilic solvents, and mixtures thereof. In a second step of the method, the ear wax solution is maintained in contact with the ear wax for a time sufficient to treat the ear wax. Preferably, the ear wax solution is held inside the ear for at least about 30 seconds, more preferably at least about 1 or 2 minutes, to increase its effectiveness. In a final step, the ear wax solution and ear wax are removed from the ear.

In another embodiment of the method, an ear wax formulation is inserted into the ear in contact with the ear wax. The ear wax formulation comprises: (a) a detergent effective to treat the ear wax by a mechanism involving at least one of dissolving the ear wax, softening the ear wax, and reducing the attachment of the ear wax to the ear, the detergent being selected from the group consisting of anionic detergents, cationic detergents, zwitterionic detergents, ampholytic detergents, amphoteric detergents, nonionic detergents having a steroid skeleton, and mixtures thereof, (b) a solvent selected from the group consisting of water, hydrophilic solvents, and mixtures thereof, and (c) a polymer effective to enhance the treatment by a mechanism involving at least one of reducing the irritancy of the detergent on the ear canal, and increasing the retention of the formulation in the ear canal and thereby reducing absorption of the formulation into the epidermal tissues of the ear canal. The ear wax formulation is maintained in contact with the ear wax for a time sufficient to treat the ear wax. Preferably, the ear wax formulation is held inside the ear for at least about 30 seconds to increase its effectiveness. Then, the ear wax formulation and the ear wax are removed from the ear.

In another embodiment of the method for removing ear wax, a first ear wax solution is inserted into the ear in contact with the ear wax. The first ear wax solution comprises: (a) a first detergent effective to loosen the ear wax, and (b) a solvent for the first detergent. The first ear wax solution is maintained in contact with the ear wax for a time sufficient to loosen the ear wax, then removed from the ear. A second ear wax solution is inserted into the ear in contact with the loosened ear wax. The second ear wax solution comprises: (a) a second detergent effective to remove the ear wax, the second detergent being different from the first detergent, and (b) a solvent for the second detergent. The second ear wax solution is maintained in contact with the ear wax for a time sufficient to enable the removal of the ear wax. Finally, the second ear wax solution and the ear wax are removed from the ear.

Various objects and advantages of this invention will become apparent to those skilled in the art from the following detailed description of the preferred embodiments.

DETAILED DESCRIPTION AND PREFERRED EMBODIMENTS OF THE INVENTION

The present invention relates to an improved ear wax solution that can be used at home or at the office of a physician or practitioner (e.g., an otologist) to improve ear hygiene and to ease ear wax removal.

The ear wax solution comprises a detergent and a solvent which is water and/or a hydrophilic solvent. The detergent is effective to treat the ear wax by a mechanism involving at least one of dissolving the ear wax, softening the ear wax, and reducing the attachment of the ear wax to the ear. The detergent is selected from anionic detergents, cationic detergents, zwitterionic detergents, ampholytic detergents, amphoteric detergents, or nonionic detergents having a steroid skeleton. Mixtures of such detergents can also be used. The detergent can be synthetic, natural, or semi-synthetic.

Suitable anionic detergents may include, but are not limited to, the following: long-chain (fatty) alcohol sulphates; alkali metal soaps, RCOOX, where X is sodium, potassium or ammonium, and R has a chain length between $C_{10}$ and $C_{20}$; alkyl aryl sulphonates; sulphonated olefins; sulphated monoglycerides; sulphated ethers; sulphated polyoxyethylated alcohols; sulphated oils; sulphosuccinates; sulphonated methyl esters; alkane sulphonates; phosphate esters; alkyl isethionates; acyl sarcosides; alkyl taurides; and fluorosurfactants. Some specific examples include sodium deoxycholate, sodium dodecyl sulphate, potassium laurate, hexadecylsulphonic acid, and sodium dioctylsulphosuccinate. In general, anionic detergents are preferred for use in the ear wax solution.

Suitable cationic detergents may include, but are not limited to, the following: hexadecyl(cetyl)trimethylammonium, dodecylpyridinium chloride, dodecylamine hydrochloride, cetyl-trimethyl-ammonium-bromide (e.g., Cetrimide B.P.), and benzalkonium chloride.

Suitable zwitterionic detergents may include, but are not limited to, the following: Zwittergent 3-08(n-octyl-N,N-dimethyl-3-ammonio-1-propanesulfonate), Zwittergent 3-10(n-decyl-N,N-dimethyl-3-ammonio-1-propanesulfonate), Zwittergent 3-12(n-dodecyl-N,N-dimethyl-3-ammonio-1-propanesulfonate) (Calbiochem, LaJolla, Calif.), and betaine and betaine-like detergents wherein the molecule contains both basic and acidic groups which form an inner salt giving the molecule both cationic and anionic hydrophilic groups (e.g., as disclosed in U.S. Pat. Nos. 2,082,275, 2,702,279 and 2,255,082).

Ampholytic and amphoteric detergents can be either cationic or anionic depending on the pH of the solution. An example of an ampholytic detergent that may be suitable in the ear wax solution is N-dodecyl-N,N-dimethyl betaine. An example of an amphoteric detergent that may be suitable is alkyl dimethylamine betaine (e.g., Empigen B B from Albright & Wilson, Richmond, Va.). Other nonlimiting examples of amphoteric and ampholytic detergents that may be suitable are dodecylbeta-alanine, N-alkyltaurines, N-higher alkylaspartic acids, and the detergents sold under the trade name "Miranol", and described in U.S. Pat. No. 2,528,378.

Preferably, the detergent is selected from the category of detergents having a steroid skeleton. Anionic detergents having a steroid skeleton may include, but are not limited to, the following: sodium deoxycholate, sodium cholate, sodium taurocholate, and sodium taurodeoxycholate. Nonionic detergents having a steroid skeleton may include, but are not limited to, the following: N,N-Bis(3-D-gluconamidopropyl)cholamide (e.g., BIGCHAP, Dojindo Molecular Technologies, Gaithersburg, Md.), N,N-Bis(3-D-gluconamidopropyl)deoxycholamide (e.g., DeoxyBIGCHAP), and digitonin. Zwitterionic detergents having a steroid skeleton may include, but are not limited to, the following:, 3[(3-Cholamidopropyl)dimethylammonio]propanesulfonic acid (e.g., CHAPS). Other categories of detergents having a steroid skeleton may also be suitable.

More preferably, the detergent having a steroid skeleton is a natural, semi-synthetic, or synthetic bile salt. Naturally occurring bile salts are biological detergents synthesized in the liver. The commonly occurring bile acids include cholic acid, deoxycholic acid, lithocholic acid, chenodeoxycholic acid, hyodeoxycholic acid, and hyocholic acid. The bile acid can be a primary or secondary bile acid. The bile salts include alkali metal salts of such acids, such as sodium deoxycholate and sodium cholate. Most preferably, the detergent is sodium deoxycholate ("DOC").

It is believed that bile salts such as DOC dissolve lipid bilayers of the ear wax by forming mixed micelles with lipids, and penetrate the monolayer of lipids bound to epidermal cells inside the ear. Approximately one-half of the constituents of ear wax accumulations in the ear are epidermal cells (mostly lipids and proteins); consequently, it is very important to remove these bound lipids to ease ear wax removal. It is also believed that the bile salts surround the hydrophobic parts of membrane bounded protein and move them into solution. By its dual action, the bile salt attaches itself to hydrophobic areas of the ear wax, exposing its hydrophilic tail into solution, and pulls hydrophobic particles such as membrane bounded protein into solution. The bile salt also denatures the protein.

Preferably, the ear wax solution contains from about 0.5% to about 10% by weight of a bile salt such as DOC, more preferably from about 0.5% to about 5%. The ear wax solution acts as an ear wax softening agent at low concentrations of detergent, and an ear wax dissolution agent at higher concentrations of detergent. For example, a 1% concentration of DOC could be used to act as an ear wax softening agent, while a higher concentration of DOC could function as an ear wax dissolution agent.

Other examples of naturally occurring detergents that may be used in the ear wax solution include phosphatides which are surface-active agents, such as lecithin and dialkylglycerylphosphorylcholine.

In another preferred embodiment of the invention, the ear wax solution contains a plurality of detergents effective to treat the ear wax by a mechanism involving at least one of dissolving the ear wax, softening the ear wax, and reducing the attachment of the ear wax to the ear. In some instances the use of two or more detergents together significantly improves the effectiveness of the ear wax solution. For example, the ear wax solution may contain a mixture of sodium deoxycholate and sodium dodecyl sulphate.

In addition to the detergent, the ear wax solution also includes a solvent for the detergent. Preferably, the solvent is water, a hydrophilic solvent, or a mixture thereof. Examples of hydrophilic solvents include alkylalcohols such as isopropanol, methanol, ethanol, n-propanol, n-butanol, secondary butanol, tertbutanol and isobutanol, alkylene glycols such as propylene glycol and polyethylene glycol, ether alcohols such as methyl cellosolve, ethyl cellosolve, propyl cellosolve, butyl cellosolve, methyl carbitol and ethyl carbitol, ether esters such as methyl cellosolve acetate and ethyl cellosolve acetate, dioxane, dimethylformamide, diacetone alcohol, methyl ethyl ketone, acetone, tetrahydrofurfuryl alcohol, and mixtures thereof. The percentage of solvent in the solution is the balance after subtracting the percentages of the other ingredients.

Preferably, the ear wax solution also includes an alkaline material effective to make the solution alkaline. An alkaline solution increases the effectiveness of the detergent. Additionally, an alkaline solution produces an expansion of keratinocytes which provides mechanical force to disintegrate ear wax. Preferably, the solution has a pH between about 7 and about 9.5. Any suitable alkaline material can be used to make the solution alkaline. Some examples of alkaline materials include the sodium, potassium, calcium, magnesium and aluminum salts of phosphoric acid, carbonic acid, citric acid, and certain aluminum/magnesium compounds. Other examples include antacid materials such as aluminum hydroxides, calcium hydroxides, magnesium hydroxides and magnesium oxide. A preferred alkaline material for use in the ear wax solution is disodium phosphate. The alkaline material may function as a buffer in addition to increasing alkalinity. Generally, the amount of alkaline material in the solution is between about 0.1% and about 5% by weight of the solution.

Preferably, the ear wax solution also includes an ionic additive effective to increase the ionic strength of the solution. An increased ionic strength increases the effectiveness of the detergent, for example, by insuring a large aggregation number and a small critical micellization concentration for the detergent. Any suitable ionic additive can be used in the solution. The ionic additive is preferably an alkali metal salt, more preferably an alkali metal salt of a halogen, even more preferably a chloride salt of an alkali material, and most preferably sodium chloride. Non-limiting examples of suitable ionic additives include sodium chloride, potassium chloride, sodium bromide, potassium bromide, sodium iodide, potassium iodide and the like. Generally, the amount of ionic additive in the solution is between about 0.1% and about 5% by weight of the solution. For example, in a preferred embodiment, sodium chloride is added to water in an amount to make a 0.1M sodium chloride solution.

In some embodiments of the invention, a polymer delivery system is added to the ear wax solution to make an improved ear wax formulation. The polymer enhances the treatment of the ear wax by reducing the irritancy of the detergent on the ear canal, and/or by increasing the retention of the formulation in the ear canal and thereby reducing absorption of the formulation into the epidermal tissues of the ear canal. These properties of the polymer allow stronger detergents to be used for ear wax removal. These properties also aid ear wax removal by increasing the ability of the formulation to wet the ear wax and the surface of the ear canal. By reducing the irritancy of the detergent on the ear canal and providing a time release delivery of the detergent, the polymer allows the use of a higher concentration of detergent without irritation of the ear. The polymer also protects and stabilizes the detergent from being broken down by any substances in the ear canal.

A current commercial product used for ear wax removal has a tendency to develop an allergic reaction in the ear. This is not a problem with the ear wax formulation of the invention. With the addition of the polymer, the ear wax formulation can usually be left inside the ear for over 30 minutes if necessary without causing an allergic reaction. The ear wax formulation is also effective to reduce tissue inflammation and exudation in the ear.

Generally, the amount of polymer in the ear wax formulation is between about 0.5% and about 20% by weight of the formulation, and typically between about 0.5% and about 10%. The polymer is usually dispersed throughout the solvent. Preferably, the polymer and other materials are formulated so that the ear wax formulation has a viscosity between about 2500 cps and about 25,000 cps. Preferably, the formulation is clear to allow for better visualization of the impacted ear wax when removing it.

The polymer delivery system can be any polymer, or combination of polymers, capable of better retaining the formulation in the ear canal and thereby reducing absorption of the formulation into the epidermal tissues of the ear canal. The polymers can be water soluble, or non-water soluble, and can come in various lengths to accommodate one's needs. Some polymers can change from a solution state to solid state dependent upon temperature. Thus, a polymer could be in solid form at room temperature, but in a solution state when heated a few degrees more.

Preferred polymers for use in the polymer delivery system include, but are not limited to, microsponge polymers, polytrap polymers, N,O-carboxymethyl-chitosan ("NOCC"), polyolprepolymers, and chitosan polymers. Microsponge polymers consist of polymeric beads having a network of pores. One such microsponge polymer is available commercially from Advanced Polymer Systems, Redwood City, Calif. The microsponge polymer is described in more detail in U.S. Pat. No. 4,690,825 to Won, issued Sep. 1, 1987, and in U.S. Pat. No. 5,145,675 to Won, issued Sep. 8, 1992 (both of which are incorporated by reference herein).

Polytrap polymers are highly cross-linked polymethacrylate copolymers. Such a polymer is manufactured by Dow Coming Corporation, Midland, Mich., and sold under the trademark Polytrap. It is powder having particles capable of absorbing high levels of lipophilic liquids and some hydrophilic liquids. The powder structure consists of a lattice of unit particles less than one micron that are fused into agglomerates of 20 to 100 microns, and the agglomerates are loosely clustered into macro-particles or aggregates of about 200 to about 1200 micron size. Advanced Polymer Systems also sells a Polytrap System which can be used in the invention.

NOCC is a chitosan derivative having carboxymethyl substituents on some of both the amino and primary hydroxyl sites of the glucosamine units of the chitosan structure. One such polymer is available commercially from Chitogenics, Inc., Halifax, Nova Scotia, Canada. This polymer is described in detail in U.S. Pat. No. 4,619,995 to Hayes, issued Oct. 28, 1986, U.S. Pat. No. 5,679,658 to Elson, issued Oct. 21, 1997, and U.S. Pat. No. 5,888,988 to Elson, issued Mar. 30, 1999 (all of which are incorporated by reference herein).

Polyolprepolymer is a mixture of liquid hydroxyl terminated polymers and polyethylene glycol. One such polymer, Polyolprepolymer-2, is available commercially from Barnet Products, Inc., Englewood Cliffs, N.J.

Chitosan is deacetylated chitin, or poly-N-acetyl-D-glucosamine. It is available commercially from many sources, such as Protan Laboratories Inc., Redmond, Wash. As used herein, "chitosan" includes chitosan, inorganic or organic salts of chitosan, and any chemically modified forms of chitosan or chitosan derivatives. This polymer is described in detail in U.S. Pat. No. 5,141,964 to Noel, issued Aug. 25, 1992, and U.S. Pat. No. 5,744,166 to Illum, issued Apr. 28, 1998 (both of which are incorporated by reference herein). Other types of polymers can also be used in the invention.

In a preferred embodiment of the invention, the ear wax solution includes one or more materials that enhance miscelle formation by the detergent. The formation of miscelles by the detergent optimizes the effectiveness of the ear wax solution. Any suitable material(s) can be used to enhance miscelle formation. In some embodiments, the materials are alkaline materials such as alkaline buffers, ionic additives and/or polymers as described above. The ear wax solution may also include one or more additives (e.g., polymers or alcohols) to increase patient comfort.

The ear wax solution, or the ear wax formulation with the polymer delivery system, can also include a topical therapeutic agent for the treatment of the ear. Some nonlimiting examples of therapeutic agents are anti-infectives, antiinflammatory agents, analgesics, and anesthetics. When the therapeutic agent is used in an ear wax formulation containing a polymer, the polymer typically enhances the formulation by either reducing side effects of the therapeutic agent, increasing the therapeutic efficacy of the therapeutic agent, or improving the stability of the formulation.

The ear wax solution of the invention can be prepared in any suitable manner. Typically, the solution is prepared by adding the ionic additive to the solvent in a desired concentration and mixing the solution, and then adding the desired amounts of alkaline material and detergent and further mixing the solution until the materials are dissolved. The ear wax formulation containing the polymer can also be prepared in any suitable manner. Typically, the formulation is prepared by initially mixing the detergent with the polymer so that it is incorporated into the polymer, and then adding the detergent/polymer to a solution prepared as described above.

In another embodiment of the method for removing ear wax, the ear is washed with a first ear wax solution to loosen the ear wax, and then a second ear wax solution is used to remove the ear wax. In this method, the first ear wax solution is inserted into the ear in contact with the ear wax. The first ear wax solution comprises: (a) a first detergent effective to loosen the ear wax, and (b) a solvent for the first detergent. The first ear wax solution is maintained in contact with the ear wax for a time sufficient to loosen the ear wax, then removed from the ear. The second ear wax solution is inserted into the ear in contact with the loosened ear wax. The second ear wax solution comprises: (a) a second detergent effective to remove the ear wax, the second detergent being different from the first detergent, and (b) a solvent for the second detergent. The second ear wax solution is maintained in contact with the ear wax for a time sufficient to enable the removal of the ear wax. Finally, the second ear wax solution and the ear wax are removed from the ear.

The following examples describe specific preferred formulations that could be made in accordance with the invention:

EXAMPLE 1

(Ear Wax Solution)

An ear wax solution according to the invention is prepared by dissolving 2% sodium deoxycholate (by weight of the solution) in water, and adding disodium phosphate and sodium chloride to the solution in amounts sufficient to provide a pH of about 8.5. A human ear wax specimen from a patient having cerumen impaction is centrifuged in the ear wax solution. Dissolution of the ear wax occurs quickly, as visualized by a yellowish color of the solution, swelling, and floating of keratin. After two to five hours approximately one-half of the ear wax is dissolved. Microscopic examination of the suspension reveals only floating dead cells and no other particles in the yellow solution.

EXAMPLE 2

(Ear Wax Formulation)

An ear wax formulation according to the invention is prepared by mixing 2% sodium deoxycholate and 2% of an acrylic acid polymer base (both by weight of the formulation) in water. Disodium phosphate and sodium chloride are added in amounts sufficient to provide the formulation with a pH of about 8.5 and a viscosity of about 15,000 cps.

The ear wax solution and ear wax formulation of the invention provide many benefits. Our work has shown that the ear wax solution quickly penetrates and dissolves the wax. As a result, the remaining ear wax is no longer cohesive and it becomes easier to be removed by gentle washing or by use of cotton swabs. In vitro tests have shown that the ear wax solution dissolves ear wax better than presently available products. In vivo tests have shown more efficient ear wax removal by the parameters tested. The ear wax solution is usually effective to dissolve ear wax in an adult male ear in less than 10 minutes to an extent that the ear wax can be easily removed by simply rinsing with water as in a shower, or by very gentle curettage by a physician, otologist, or trained nurse.

The ear wax solution dissolves ear wax enough to make lavage or instrument removal less difficult, less painful, and with no bleeding. The solution allows removal of impacted earwax that resists instrument removal. The solution will greatly reduce the cost of ear wax removal as there will be less need for irrigation or direct removal of ear wax by physicians, as the solution will dissolve ear wax with just direct application and flushing the debris out of the ear canal with water. Some advantages of the ear wax solution are low cost, effectiveness, and safety for use in patient care. Trauma to the ear drum and ear canal may occur when a physician or otologist curettes or suctions impacted ear wax blindly without being able to properly see the anatomical structures clearly. This will be greatly reduced by the use of the ear wax solution which dissolves the ear wax, greatly increasing visualization. The ear wax solution will maximize patient comfort and convenience in ear wax removal, which should increase patients' compliance with the process of ear wax removal (which is difficult in young children especially).

The ear wax solution will reduce hearing loss and ear infection secondary to untreated ear wax impaction. Ear wax impaction is a reversible cause of conduction hearing loss, particularly in the elderly. Ear wax impaction also provides ideal conditions for the growth of microorganisms: warmth, darkness, moisture, stagnation, and the presence of debris and nutrients in the ear. The ear wax solution will effectively alleviate these problems.

The ear wax solution can be beneficial for ear hygiene to eliminate build up of ear wax in the ear. This could be used in patients prone to ear problems due to ear wax as a prophylaxis similar to the use of dental floss for dental hygiene.

Further, the ear wax solution could be used with patients following trauma to the ear, which may result in debris in the ear including ear wax, blood, or external solutions. Such debris can be completely or partially dissolved by the ear wax solution to allow visualization of the ear drum and ear canal to assess the problem.

The principle and mode of operation of this invention have been described in its preferred embodiments. However, it should be noted that this invention may be practiced otherwise than as specifically described without departing from its scope.

What is claimed is:

1. An ear wax solution consisting essentially of:
   a detergent effective to treat the ear wax by a mechanism involving at least one of dissolving the ear wax, softening the ear wax, and reducing the attachment of the ear wax to the ear, wherein said detergent is a salt of a bile acid;
   a solvent selected from the group consisting of water, hydrophilic solvents, and mixtures thereof;
   an alkaline material effective to make the solution alkaline; and
   an ionic additive effective to increase the ionic strength of the solution.

2. An ear wax solution according to claim 1 wherein the detergent is sodium deoxycholate.

3. An ear wax solution comprising:
   a detergent comprising a salt of a bile acid as only active agent, the detergent being effective to treat the ear wax by a mechanism involving at least one of dissolving the ear wax, softening the ear wax, and reducing the attachment of the ear wax to the ear;
   a solvent selected from the group consisting of water, hydrophilic solvents, and mixtures thereof; and
   an alkaline material effective to make the solution alkaline.

4. An ear wax solution according to claim 3 wherein the detergent is sodium deoxycholate.

5. An ear wax formulation consisting essentially of:
   a detergent effective to treat the ear wax by a mechanism involving at least one of dissolving the ear wax, softening the ear wax, and reducing the attachment of the ear wax to the ear, wherein said detergent is a salt of a bile acid;
   a polymer effective to enhance the treatment by a mechanism involving at least one of reducing the irritancy of the detergent on the ear canal, and increasing the retention of the formulation in the ear canal and thereby reducing absorption of the formulation into the epidermal tissues of the ear canal; and
   a solvent selected from the group consisting of water, hydrophilic solvents, and mixtures thereof.

6. An ear wax formulation according to claim 5 wherein the detergent is sodium deoxycholate.

7. An ear wax formulation according to claim 5 further comprising an alkaline material effective to make the formulation alkaline.

8. An ear wax formulation according to claim 5 further comprising an ionic additive effective to increase the ionic strength of the formulation.

9. A method for removing ear wax from an ear, comprising the steps of:
   inserting an ear wax solution into the ear in contact with the ear wax, the ear wax solution consisting essentially of: (a) a detergent effective to treat the ear wax by a mechanism involving at least one of dissolving the ear wax, softening the ear wax, and reducing the attachment of the ear wax to the ear, wherein said detergent is a salt of a bile acid, and (b) a solvent selected from the group consisting of water, hydrophilic solvents, and mixtures thereof;
   maintaining the ear wax solution in contact with the ear wax for a time sufficient to treat the ear wax; and
   removing the ear wax solution and ear wax from the ear.

10. A method according to claim 9 wherein the ear wax solution is held inside the ear for at least about 30 seconds before removing it from the ear, to increase its effectiveness.

11. A method for removing ear wax from an ear, comprising the steps of:
   inserting an ear wax formulation into the ear in contact with the ear wax, the ear wax formulation consisting essentially of: (a) a detergent effective to treat the ear wax by a mechanism involving at least one of dissolving the ear wax, softening the ear wax, and reducing the attachment of the ear wax to the ear, wherein said detergent is a salt of a bile acid, (b) a solvent selected from the group consisting of water, hydrophilic solvents, and mixtures thereof, and (c) a polymer effective to enhance the treatment by a mechanism involving at least one of reducing the irritancy of the detergent on the ear canal, and increasing the retention of the formulation in the ear canal and thereby reducing absorption of the formulation into the epidermal tissues of the ear canal;
   maintaining the ear wax formulation in contact with the ear wax for a time sufficient to treat the ear wax; and
   removing the ear wax formulation and the ear wax from the ear.

12. A method according to claim 11 wherein the ear wax formulation is held inside the ear for at least about 30 seconds before removing it from the ear, to increase its effectiveness.

13. An ear wax solution consisting essentially of:
   a detergent effective to treat the ear wax by a mechanism involving at least one of dissolving the ear wax, softening the ear wax, and reducing the attachment of the ear wax to the ear wherein said detergent is a salt of a bile acid;
   a solvent for the ear wax; and
   a material that enhance miscelle formation by the detergent to increase the effectiveness of the solution.

* * * * *